US008897786B2

(12) United States Patent
Ryu et al.

(10) Patent No.: US 8,897,786 B2
(45) Date of Patent: Nov. 25, 2014

(54) SERVICE CONNECTION APPARATUS AND METHOD IN PORTABLE TERMINAL

(71) Applicant: Samsung Electronics Co. Ltd., Suwon-si, Gyeonggi-do (KR)

(72) Inventors: Dong Won Ryu, Seoul (KR); Euy Beom Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/027,634

(22) Filed: Sep. 16, 2013

(65) Prior Publication Data

US 2014/0018078 A1    Jan. 16, 2014

Related U.S. Application Data

(63) Continuation-in-part of application No. 13/923,648, filed on Jun. 21, 2013, and a continuation of application No. 12/329,362, filed on Dec. 5, 2008, now Pat. No. 8,472,957.

(30) Foreign Application Priority Data

Dec. 24, 2007  (KR) .................. 10-2007-0136078

(51) Int. Cl.
*H04W 36/00* (2009.01)
(52) U.S. Cl.
USPC ............ 455/436; 455/437; 455/438; 455/439

(58) Field of Classification Search
USPC .................................. 455/436–439
See application file for complete search history.

(56) References Cited

U.S. PATENT DOCUMENTS

| | | | |
|---|---|---|---|
| 6,510,219 B1 * | 1/2003 | Wellard et al. ........... 379/221.01 |
| 7,072,311 B1 | 7/2006 | Czaja et al. | |
| 7,162,236 B2 * | 1/2007 | Dorenbosch et al. ...... 455/432.1 |
| 7,526,313 B2 * | 4/2009 | Mousseau et al. ......... 455/552.1 |
| 7,639,649 B2 | 12/2009 | Czaja et al. | |
| 7,693,522 B2 | 4/2010 | Bichot et al. | |
| 7,818,003 B2 | 10/2010 | Callaghan | |
| 8,447,303 B2 * | 5/2013 | Gisby et al. .................. 455/436 |
| 8,472,957 B2 * | 6/2013 | Ryu et al. ...................... 455/436 |
| 2004/0218575 A1 * | 11/2004 | Ibe et al. ........................ 370/338 |
| 2004/0266426 A1 * | 12/2004 | Marsh et al. ............... 455/426.2 |
| 2005/0107086 A1 * | 5/2005 | Tell et al. ...................... 455/445 |
| 2005/0239444 A1 | 10/2005 | Shieh | |

FOREIGN PATENT DOCUMENTS

| KR | 10-2006-0031125 A | 4/2006 |
|---|---|---|
| KR | 10-0752138 A | 8/2007 |

* cited by examiner

*Primary Examiner* — Kenneth B. Wells
(74) *Attorney, Agent, or Firm* — Jefferson IP Law, LLP

(57) ABSTRACT

A call connection method and apparatus are disclosed. When a service is released in a portable terminal that supports different communication modes due to a network problem, the call connection method and apparatus reconnects the service to another network. The call connection method includes performing a first service through a first network, analyzing, when the connected first service is released, the cause of disconnection, acquiring, when the cause of disconnection is a problem in the first network, connection information, and attempting to connect a second service through a second network based on the connection information.

20 Claims, 2 Drawing Sheets

US 8,897,786 B2

SERVICE CONNECTION APPARATUS AND METHOD IN PORTABLE TERMINAL

PRIORITY

This application is a continuation of prior application Ser. No. 13/923,648, filed on Jun. 21, 2013, which is a continuation of U.S. Pat. No. 8,472,957 issued on Jun. 25, 2013, which claimed the benefit under 35 U.S.C. §119(a) of a Korean patent application filed on Dec. 24, 2007 in the Korean Intellectual Property Office and assigned Serial No. 10-2007-0136078, the entire disclosures of each of which are hereby incorporated by reference.

BACKGROUND OF THE INVENTION

1. Field of the Invention

The present invention relates to call connection technology. More particularly, the present invention relates to a method and apparatus for attempting to reconnect a call when a call drop occurs in a portable terminal that can support different communication modes.

2. Description of the Related Art

As the popularity of portable terminals continues to increase, manufacturers are developing a variety of functions to satisfy additional user demands. As an example, multi-mode portable terminals have recently appeared on the market. A multi-mode portable terminal is a terminal that can use two or more wireless communication networks.

Conventional portable terminals that support one type of wireless communication network can perform communication within only a corresponding wireless communication network service area. In contrast, the multi-mode portable terminals can perform communication within two or more wireless communication network service areas. For example, dual mode portable terminals can support a Code Division Multiple Access (CDMA) network and a Global System for Mobile communication (GSM) network, so that they can perform communication within both CDMA and GSM network service areas. Accordingly, the dual mode portable terminals can be more widely used than the single mode portable terminals.

However, since the conventional multi-mode portable terminals switch between networks in such a way that they are booted, enter an idle mode, and then perform communication by operation of their menu, they are complicated to operate and require significant time to switch their modes. To resolve these problems, a multi-standby portable terminal has been proposed. The multi-standby portable terminal, unlike the multi-mode portable terminals, can simultaneously support two networks, for example, a CDMA network and a GSM network.

Wireless communication systems, which employ the $2^{nd}$ generation communication mode, such as a GSM communication mode and a CDMA communication mode, have been used in a wide service area for several years. Accordingly, the basic facilities that support the $2^{nd}$ generation communication mode have been constructed and are well established.

On the other hand, in order to provide services that a wireless communication system of the $2^{nd}$ generation communication mode (hereinafter referred to as a '$2^{nd}$ generation network') cannot support, a wireless communication system adopting the $3^{rd}$ generation communication mode (hereinafter referred to as a '$3^{rd}$ generation network'), such as CDMA 2000 communication, Wideband Code Division Multiple Access (WCDMA) communication, etc., is being gradually introduced. In an area equipped with the $3^{rd}$ generation network, the wireless systems can use the basic facilities for the $2^{nd}$ generation network and support specialized communication of the $3^{rd}$ generation network.

However, the $3^{rd}$ generation network is less widely constructed than the $2^{nd}$ generation network. In particular, there are still many weak electric field areas and no service areas, with respect to the $3^{rd}$ generation network. Therefore, when users use a specialized service of the $3^{rd}$ generation network, for example, a Video Telephony (VT) call service, they frequently experience a call drop when traveling to a weak electric field area or to an area with no service.

That is, while a service, such as a VT call service, is performed through the $3^{rd}$ generation network, a call drop frequently occurs due to gap areas. In addition, when a portable terminal using a VT call service is moved from the coverage of the $3^{rd}$ generation network to a service area where only the $2^{nd}$ generation network is available, its VT call is disconnected.

When call connection is dropped and therefore terminated during the VT call service, a user attempts to manually reconnect the call. That is, when connection of the VT call is enforcedly terminated, the user attempts to connect the disconnected VT call again, without knowing the cause of disconnection. However, when the user moves out of the $3^{rd}$ generation network service area, the call connection fails and thus the user must attempt to reconnect a voice call using the $2^{nd}$ generation network.

SUMMARY OF THE INVENTION

An aspect of the present invention is to address at least the above-mentioned problems and/or disadvantages and to provide at least the advantages described below. Accordingly, an aspect of the present invention is to provide a method and apparatus for reconnecting a call when a connected call is released in portable terminals providing different communication services.

Another aspect of the present invention is to provide a method and apparatus for reconnecting a call when a call drop occurs in portable terminals providing different communication modes.

Yet another aspect of the present invention is to provide a method and apparatus that can automatically connect a Video Telephony (VT) call of the $3^{rd}$ generation network to a voice call of the $2^{nd}$ generation network when a call drop of the VT call occurs, thereby providing the user with convenient use and continuous services.

In accordance with an exemplary embodiment of the present invention, a call connection method in a portable terminal that supports communication modes of different networks is provided. The method includes performing a first service through a first network, analyzing, when the connected first service is released, the cause of disconnection, acquiring, when the disconnection cause is a problem in the first network, connection information and attempting to connect a second service through a second network based on the connection information.

In accordance with another exemplary embodiment of the present invention, a call connection method in a portable terminal that supports a communication mode of different networks is provided. The method includes performing a video telephony call with a target portable terminal through a $3^{rd}$ generation network, analyzing, when the connected video telephony call is disconnected, a disconnection cause, acquiring, when the disconnection cause is a problem in the $3^{rd}$ generation network, connection information about the target portable terminal, and attempting to connect a voice call through a $2^{nd}$ generation network based on the connection information.

In accordance with yet another exemplary embodiment of the present invention, a portable terminal that supports a communication mode of different networks is provided. The terminal includes a first communication module for establishing a communication channel with a $2^{nd}$ generation network and for providing a voice call service, a second communication module for establishing a communication channel with a $3^{rd}$ generation network and for providing a video telephony service, a memory for storing information about a service disconnection cause, guide information according to a new service connection attempt that is performed as the connected service is released, and connection information of a target portable terminal that is connected to the service; and a controller for processing a voice call service of the $2^{nd}$ generation network through the first communication module and a video telephony service of the $3^{rd}$ generation network through the second communication module and for connecting, when a service is connected to a target portable terminal through one of the $2^{nd}$ and $3^{rd}$ generation networks, the released service to another network that is different from the network before the service is released.

BRIEF DESCRIPTION OF THE DRAWINGS

The above and other aspects, features and advantages of certain exemplary embodiments of the present invention will be more apparent from the following description taken in conjunction with the accompanying drawings, in which.

Throughout the drawings, it should be noted that like reference numbers are used to depict the same or similar elements, features and structures.

DETAILED DESCRIPTION OF EXEMPLARY EMBODIMENTS

Figure 1:
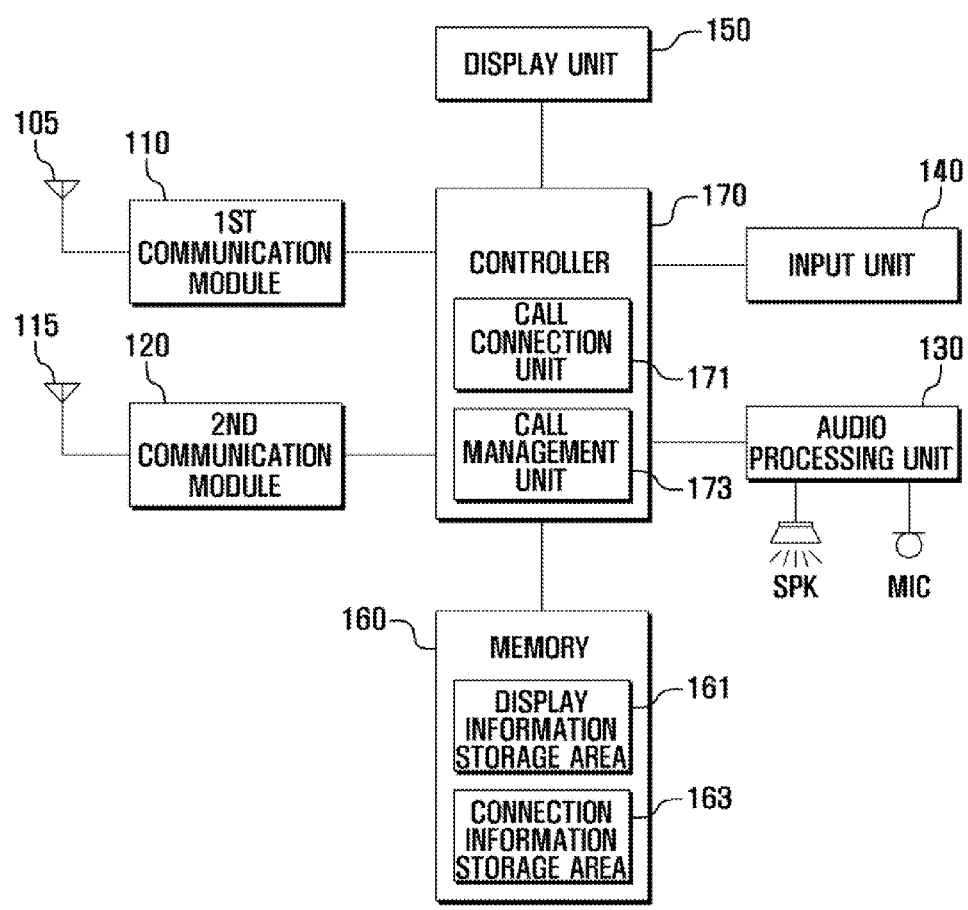
FIG. 1 is a schematic block diagram illustrating a portable terminal according to an exemplary embodiment of the present invention.

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Exemplary embodiments of the present invention are related to a method and apparatus that can automatically reconnect a call when a call drop of the connected call occurs in a portable terminal providing different communication modes. In particular, when a call drop of a Video Telephony (VT) call occurs unexpectedly, for example due to deterioration of an electric field in a wireless service area, an exemplary method and apparatus of the present invention can automatically perform call connection of a voice call. That is, when a connected call of a VT call is disconnected due to various causes, for example, the deterioration of the electric field of a $3^{rd}$ generation network, an exemplary method and apparatus of the present invention can automatically connect a voice call to a target portable terminal through a $2^{nd}$ generation network.

In the following description, exemplary embodiments of the present invention are described based on portable terminals that support wireless communication systems of the $2^{nd}$ generation communication mode (hereinafter referred to as a '$2^{nd}$ generation network'), such as Global System for Mobile communication (GSM) and Code Division Multiple Access (CDMA), and wireless communication systems of the $3^{rd}$ generation communication mode (hereinafter referred to as a '$3^{rd}$ generation network'), such as, Code Division Multiple Access 2000 (CDMA 2000) communication mode, and Wideband Code Division Multiple Access (WCDMA) communication mode. However, it should be understood that the present invention is not limited to the networks described above. That is, the present invention can be applied to portable terminals that support other types of communication modes.

FIG. 1 is a schematic block diagram illustrating a portable terminal according to an exemplary embodiment of the present invention The portable terminal includes two slots that support the $2^{nd}$ and $3^{rd}$ generation networks and communications therewith, respectively, when the $2^{nd}$ and $3^{rd}$ generation network cards are installed into the slots. Of course, it is understood that the present invention is not limited to the present exemplary embodiment. For example, the portable terminal may be implemented in such a way that a dual card supporting the $2^{nd}$ and $3^{rd}$ generation networks may be installed in a single slot or that more than two slots may be provided for various networks. That is, the present invention is not limited in its application to the $2^{nd}$ and $3^{rd}$ generation networks.

As illustrated in FIG. 1, the portable terminal adapted to the functions of the present invention includes a first antenna 105, a first communication module 110 for providing the $2^{nd}$ generation communication service, a second antenna 115, a second communication module 120 for providing the $3^{rd}$ communication service, an audio processing unit 130, an input unit 140, a display unit 150, a memory 160 and a controller 170.

Referring to FIG. 1, the first antenna 105 establishes a communication channel with the $2^{nd}$ generation network and processes transmitted/received signals of a frequency band for the $2^{nd}$ generation communication service. The second antenna 115 establishes a communication channel with the $3^{rd}$ generation network and processes transmitted/received signals of a frequency band for the $3^{rd}$ generation communication service.

The first communication module 110 performs wireless communication through the first antenna 105. It establishes a communication channel with the $2^{nd}$ generation network through the first antenna 105 and transmits/receives Radio Frequency (RF) signals of a frequency band supported by the $2^{nd}$ generation network. The first communication module 110 includes an RF transmitter for up-converting the frequency of transmitted signals and amplifying the transmitted signals. The first communication module 110 also includes an RF receiver for low-noise amplifying received RF signals and down-converting the received RF signals.

The second communication module 120 performs wireless communication through the second antenna 115. It establishes a communication channel with the $3^{rd}$ generation network through the second antenna 115 and transmits/receives RF signals of a frequency band supported by the $3^{rd}$ generation network. The second communication module 120 includes an RF transmitter for up-converting the frequency of transmitted signals and amplifying the transmitted signals. The second communication module 120 also includes an RF receiver for low-noise amplifying received RF signals and down-converting the received RF signals.

The audio processing unit 130 is provided to play back audio signals received from the controller 170 and to provide externally received audio signals as input to the controller 170. That is, the audio processing unit 130 converts audio signals received from the controller 170 into audible sound and outputs them through a speaker SPK. In addition, the audio processing unit 130 converts audio signals received by a microphone MIC, such as voice signals, into data and outputs them to the controller 170.

The input unit 140 serves to receive information input by a user and output the information to the controller 170. The input unit 140 may include a plurality of function, number and other keys and receive input about a variety of characters and other functions through the key signals, related to function settings and function control of the portable terminal. In an exemplary implementation, the input unit 140 is formed having a touch pad, a general key arrayed pad, a QWERTY key array pad, or a combination thereof.

The memory 160 stores at least one application program necessary for the functions according to exemplary embodiments of the present invention. The memory 160 also stores user data generated by a user, data received from one of the networks, information generated as the application is executed and the like. It may also include one or more buffers that store data generated as an application is executed.

In an exemplary implementation, the memory 160 may include a display information storage area 161 and a connection information storage area 163. In an exemplary implementation, the display information storage area 161 stores pop-up messages, for example, guide information showing that a connected call is released due to deterioration of the electric field (i.e. poor signal strength) of a network. The connection information storage area 163 buffers call connection information of a target portable terminal when a call connected to the target terminal is disconnected. In an exemplary implementation, the connection information storage area 163 buffers the phone number of the target portable terminal, information about the network to which the target portable terminal is connected, and the like. The connection information storage area 163 supplies the call connection information to the controller 170, for example at the request of the controller 170, when a call connection is attempted again.

In an exemplary implementation, the guide information may be a pop-up message showing a standby request that is caused as a connected call is disconnected due to a deterioration of the electric field of the $3^{rd}$ generation network (e.g. a deterioration caused by entering a gap area, leaving the coverage area of the $3^{rd}$ generation network, and so on), and thus a new call is attempted through the $2^{nd}$ generation network.

The display unit 150 displays screen data generated when the application is executed, data generated by the user's key operation states, by the function setting information, etc. The display unit 150 may be implemented with an LCD and the LCD may include a touch screen. In that case, the input unit 150 may provide some or all of the functions of the input unit 140. Furthermore, the display unit 150 may display guide information from the display information storage area 163, through a pop-up method, according to the control of the controller 170.

The controller 170 controls the operation of the portable terminal. It also controls signal flows between the elements in the portable terminal, such as the first and second communication modules 110 and 120, the audio processing unit 130, the input unit 140, the memory 160, and the display unit 150. It also includes a data processor that includes a codec and a modem.

In particular, the controller 170, according to exemplary embodiments of the present invention, controls the connection of a voice call through the $2^{nd}$ generation network and the connection of a video telephony call through the $3^{rd}$ generation network. When a call connected to a particular target portable terminal is disconnected, the controller 170 analyzes the call disconnection cause. If the controller 170 ascertains that the call disconnection is caused by the network, it attempts to connect a new call to the particular target portable terminal using another network as opposed to the currently disconnected network. While new call connection is attempted, the controller 170 may display a pop-up message showing the determined call disconnection cause and showing that a new call connection is attempted.

For example, if a VT call service, provided to a particular portable terminal through the $3^{rd}$ generation network, is released, the controller 170 controls to be connected to a voice call service, based on the connection information of the particular portable terminal through the $2^{nd}$ generation network. It should be understood that the control algorithm of the controller 170 can be activated or inactivated according to a user's function settings.

In order to efficiently perform the function described above, the controller 170 may include a call connection unit 171 and a call management unit 173.

The call connection unit 171 processes the connection of a voice call service through the $2^{nd}$ generation network and the connection of a VT call service through the $3^{rd}$ generation network. In particular, when the connected service is released, the call connection unit 171 processes a new connection service, according to the disconnection causes, so that the connection can be connected not to the currently disconnected network but to another network. The call connection unit 171 can process the new service connection, referring to connection information in the connection information storage area 165.

When the connected service is released, the call management unit 173 analyzes the disconnection cause. If the call management unit 173 ascertains that the disconnection is caused by the network, it provides the information to the call connection unit 171.

Although a portable terminal according to an exemplary embodiment of the present invention is schematically shown in FIG. 1 for convenience, it should be understood that the present invention is not limited to the present embodiment. For example, the portable terminal may further include a camera module, an electronic payment module, a digital broadcasting module, a short-range communication module, a battery module, etc. It will also be easily appreciated to those skilled in the art that a portable terminal according to the present invention can be configured to remove one or more elements from the configuration described above or to replace them with other elements.

In the following description, a call connection method according to an exemplary embodiment of the present invention is explained. It should be understood that the present invention is not limited to the illustrated embodiment and that there are many modifications from the present example.

Figure 2:
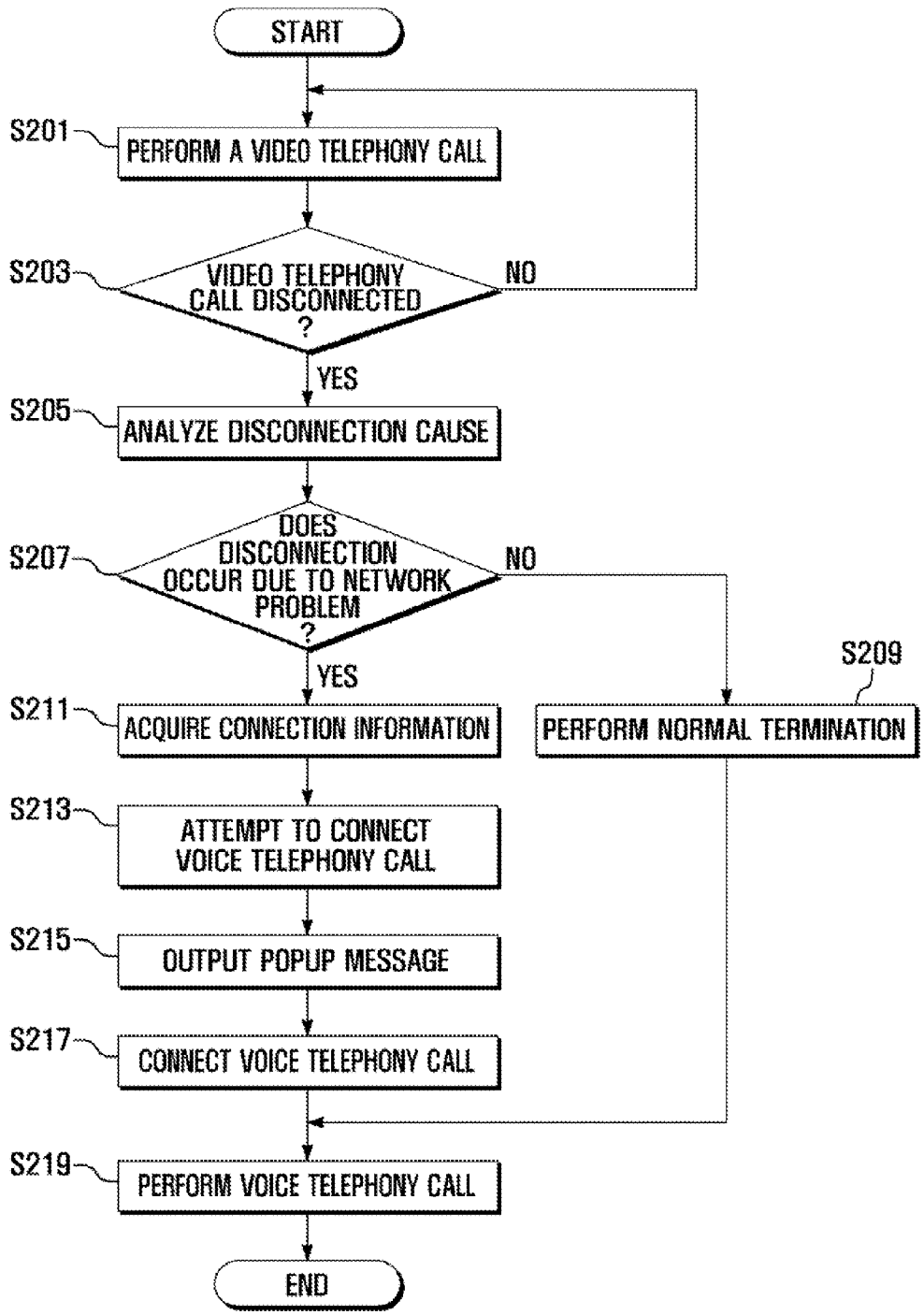
FIG. 2 is a flowchart describing a method for connecting a new call when a connected call is released in a portable terminal, according to an exemplary embodiment of the present invention.

FIG. 2 is a flowchart describing a method for connecting a new call when a connected call is released in a portable terminal according to an exemplary embodiment of the present invention. In the following description, it is assumed that a function according to the present invention is previously activated by a user. That is, the function of the present invention may be activated/inactivated by a user. Therefore, the procedure of FIG. 2 may further include a step of determining whether a function is activated.

Referring to FIG. 2, the controller of a portable terminal performs a VT call with a target portable terminal in step S201. The controller determines whether a VT call is disconnected during the process of the VT call in step S203.

If it is determined that the VT call is disconnected in step S203, the controller analyzes the cause of disconnection of the VT call in step S205 and then determines whether the disconnection is caused by the network in step S207. More specifically, the cause of disconnection is analyzed to determine whether the disconnection was performed at the user's request or the request of the target portable terminal or whether the disconnection was caused by the network of the VT call (i.e. the $3^{rd}$ generation network).

The call disconnection by the network may occur when an electric field strength deteriorates as a portable terminal, in a call connection with a target portable terminal, enters a gap area, and thus a call drop occurs by radio link failure. A call drop may also occur due to various types of handover failures, such as a network malfunction regarding synchronization. These network problems can be ascertained by evaluating the strength of a signal received from a base station.

When the controller ascertains what the call disconnection is performed under the direction of the user, that is, under normal circumstances, at step S207, it normally terminates the call in step S209. On the contrary, when the controller ascertains that the call disconnection is caused by a network problem, it acquires connection information about the target portable terminal in step S211.

In step S213, the controller establishes a communication channel with another network (e.g. the $2^{nd}$ generation network) and attempts to connect a voice call, based on the acquired connection information. While the controller is being connected to a voice call, it can display a previously set pop-up message on the display unit in step S215.

When the voice call is connected to the target portable terminal in step S217, the controller processes operations related to the voice call with the target portable terminal in step S219.

Although not illustrated in FIG. 2, when the portable terminal is connected to a target portable terminal to perform service connection, a method according to an exemplary implementation may further include the processes of acquiring and storing information about the target portable terminal and information about a corresponding network through which the service connection trial is performed. It will also be appreciated that after attempting to connect a voice call at step S213, the process of outputting a pop-up message may be omitted according to a user's setting or the initial setting of the portable terminal.

As described above, according to an exemplary embodiment of the present invention, when a connected VT call is disconnected, the disconnected call is automatically connected to a voice call. However, the exemplary embodiment shown in FIG. 2 may be variously modified in such a way that, when a connected voice call is disconnected, a new voice call is automatically connected or a new VT call is automatically connected. It may also be modified in such a way that, when a connected VT call is disconnected, a new VT call is automatically connected.

In an exemplary embodiment of the present invention, a new call is connected through another network that is not the previously connected network. However, it will be appreciated that a new call can also be connected through the same network.

As described above, in a method and apparatus for connecting a call in a portable terminal according to exemplary embodiments of the present invention, when a portable terminal supporting different communication modes fails call connection in one of the communication modes, it switches the current communication mode to another communication mode and attempts to connect a call again, thereby enhancing the success rate of call connection. In particular, when a call drop occurs in a portable terminal supporting different communication modes, call connection can be easily attempted again. When a call drop of a connected VT call using the $3^{rd}$ generation network occurs, it is automatically connected to a voice call using the $2^{nd}$ generation network, thereby providing a user with greater convenience and continuous service.

While the invention has been shown and described with reference to exemplary embodiments thereof, it will be understood by those skilled in the art, that various changes in form and details may be made therein without departing from the spirit and scope of the invention as defined in the appended claims and their equivalents.

What is claimed is:

1. A method comprising:
providing, at a user device, a packet switched service via a first cellular network in response to a service request;
connecting the user device with a second cellular network based on a determination that a signal quality corresponding to the first cellular network has deteriorated below a specified value; and
providing, at the user device, a circuit switched service via the second cellular network in relation with the service request.

2. The method of claim 1, wherein the providing of the circuit switched service comprises:
selecting the first cellular network from a plurality of networks available to the user device, the plurality of networks including the first cellular network and the second cellular network.

3. The method of claim 1, wherein the providing of the circuit switched service comprises:
disconnecting the user device from the first cellular network.

4. The method of claim 1, wherein the connecting of the user device with the second cellular network comprises:
evaluating strength of a signal received from the first cellular network in relation with the packet switched service as the signal quality.

5. The method of claim 1, wherein the connecting of the user device with the second cellular network comprises:

comparing the signal quality with at least one of a first specified value and another signal quality corresponding to the second cellular network.

6. The method of claim 1, wherein the connecting of the user device with the second cellular network comprises:
acquiring connection information associated with the circuit switched service from the first cellular network; and
establishing a connection with the second cellular network based at least in part on the connection information.

7. The method of claim 1, further comprising:
evaluating another signal quality corresponding to the second cellular network; and
determining whether to release the circuit switched service or to disconnect the user device from the second cellular network based at least in part on the evaluation.

8. The method of claim 1, wherein the providing of the packet switched service comprises:
presenting information associated with the packet switched service via the user device.

9. The method of claim 8, wherein the presenting of the information comprises:
presenting a cause of release of the packet switched service or disconnection of the user device from the first cellular network as the information.

10. The method of claim 1, wherein the packet switched service comprises a first communication mode, and
wherein the circuit switched service comprises a second communication mode different from the first communication mode.

11. The method of claim 10, wherein the first communication mode comprises a video telephony call and the second communication mode comprises a voice call.

12. An apparatus comprising:
a processor-implemented controller configured to:
provide, in response to a service request, a packet switched service via a first cellular network;
connect the apparatus with a second cellular network based on a determination that a signal quality corresponding to the first cellular network has deteriorated below a specified value; and
provide a circuit switched service via the second cellular network in relation with the service request.

13. The apparatus of claim 12, wherein the processor-implemented controller is configured to:
release the packet switched service or disconnect from the first cellular network based at least in part on the signal quality.

14. The apparatus of claim 12, wherein the processor-implemented controller is configured to:
evaluate a strength of a signal received from the first cellular network as the signal quality.

15. The apparatus of claim 12, wherein the processor-implemented controller is configured to:
compare the signal quality with at least one of a specified value and another signal quality corresponding to the second cellular network.

16. The apparatus of claim 12, wherein the processor-implemented controller is configured to:
acquire connection information associated with the circuit switched service from the first network.

17. The apparatus of claim 12, wherein
the processor-implemented controller is configured to:
select the first cellular network from a plurality of networks available to the apparatus, the plurality of networks including the first cellular network and the second cellular network.

18. The apparatus of claim 12, wherein the processor-implemented controller is configured to:
display information associated with at least one of the packet switched service and the circuit switched service via a display operatively coupled to the apparatus.

19. The apparatus of claim 12, wherein the packet switched service comprises a video telephony call and the circuit switched service comprises a voice call.

20. A non-transitory computer-readable storage medium storing instructions that, when executed by one or more processors, cause the one or more processors to perform operations comprising:
providing, at a user device, a packet switched service via a first cellular network in response to a service request;
connecting the user device to a second cellular network based on a determination that a signal quality corresponding to the first cellular network has deteriorated below a specified value; and
providing, at the user device, a circuit switched service via the second cellular network in relation with the service request.

* * * * *